United States Patent [19]
Perry

[11] Patent Number: 5,916,552
[45] Date of Patent: Jun. 29, 1999

[54] DEER URINE ATTRACTANT COMPOSITION METHOD OF MAKING AND USING

[76] Inventor: Mark D. Perry, 2504 LeHommeDiev View NE., Alexandria, Minn. 56308

[21] Appl. No.: 09/027,750

[22] Filed: Feb. 23, 1998

[51] Int. Cl.[6] .......................... A01N 25/00; A01N 25/04; A01N 63/00; A01K 35/22
[52] U.S. Cl. .......................... 424/84; 424/400; 424/484; 424/545; 424/546; 514/944; 514/964; 43/1
[58] Field of Search .............................. 424/84, 400, 484, 424/545, 546; 514/944, 964; 43/1

[56] References Cited

U.S. PATENT DOCUMENTS

| | | | |
|---|---|---|---|
| 4,160,834 | 7/1979 | Inazuka et al. | 424/84 |
| 4,205,066 | 5/1980 | Hennart et al. | 424/84 |
| 4,487,759 | 12/1984 | Nesbitt et al. | 424/32 |
| 4,667,430 | 5/1987 | Ziese, Jr. | 43/1 |
| 4,944,940 | 7/1990 | Christenson, II | 424/84 |
| 4,953,763 | 9/1990 | Kierum et al. | 222/644 |
| 4,990,514 | 2/1991 | Bruey | 514/275 |
| 5,263,274 | 11/1993 | Speed | 43/1 |
| 5,307,584 | 5/1994 | Jarvis | 43/1 |
| 5,327,667 | 7/1994 | Fore | 43/1 |
| 5,369,903 | 12/1994 | Cox | 43/1 |
| 5,429,271 | 7/1995 | Porter | 222/3 |
| 5,456,036 | 10/1995 | Butz | 43/1 |
| 5,465,521 | 11/1995 | Baker et al. | 43/1 |
| 5,555,665 | 9/1996 | Fore | 43/1 |
| 5,565,111 | 10/1996 | Newman | 210/774 |
| 5,611,165 | 3/1997 | Blaha | 43/1 |
| 5,622,314 | 4/1997 | Eason | 239/47 |
| 5,672,342 | 9/1997 | Bell | 417/84 |

*Primary Examiner*—John Pak
*Attorney, Agent, or Firm*—Tipton L. Randall

[57] ABSTRACT

A semi-solid deer attractant lure comprised of liquid deer urine plus a sufficient amount of flavorless gelatin to produce a semi-solid rubbery composition is disclosed. Also disclosed is a method of making and a method of using the deer attractant lure composition.

4 Claims, No Drawings

DEER URINE ATTRACTANT COMPOSITION METHOD OF MAKING AND USING

FIELD OF THE INVENTION

The invention relates to a game animal urine attractant composition, and more particularly to a deer urine attractant composition, as well as a method of making and using the composition.

BACKGROUND OF THE INVENTION

Hunting wild animals, and especially deer, is an art requiring the proper mix of intelligence, patience, endurance and the right equipment. Because deer rely heavily on their highly developed sense of smell to alert them to a multitude of factors, such as danger, food, the presence of other animals, it is necessary for the hunter to blend into the environment, without alerting the deer to his presence. It is also very helpful to provide some means to attract the animal to the hunter's vicinity.

With respect to deer, and especially the male of the species or the buck, a buck lure is often used to tempt the buck. Buck lures have application not only for deer hunters, but also for photographers and other wildlife enthusiasts.

Generally, animal scents are liquids sold in small bottles. The hunter disperses the scent in the selected hunting area. The scent is generously applied to an elevated scent pad disposed in an artificial scrape surrounding an artificial rub, that preferably is approximately 24 inches above ground, as well as on the artificial rub. Alternatively, a "scent bomb" is placed on the ground or no higher than 24 inches off the ground. A "scent bomb" is made by pouring the scent into a 35 mm film canister filled with an elongated strip of clean cotton. The film canister is capped tightly to tightly seal the scent for transport to the hunting area. At the hunting sight canisters are placed at selected positions upwind of the stand, the cap is removed and, with a stick or other elongated object, a portion of the scent-soaked strip of cotton is removed from the canister and draped along the side of the container. At the end of a day's hunt the scent-soaked cotton is pushed back into the storage canister, again using a stick or the like, and the container is recapped.

Several problems arise from the above method of dispersing a game scent. Filling the canister with scent and draping the strip of cotton cloth over the side is messy and inconvenient. Many of the scents have an odor that is pungent to humans and difficult to remove from skin and clothing; therefore inordinate care in handling is required. Also, the cotton strips dry out quickly and can freeze in cold weather.

A number of innovations have been developed relating to the problem of dispersing animal scent at a specific location. The following U.S. patents are representative of some of those innovations.

Christenson, II in U.S. Pat. No. 4,944,940 discloses a buck lure that includes a deer tarsal gland and a fluid in which the predominant ingredient is deer urine. Other ingredients include essence of deer interdigital gland, essence of deer femoral gland and a preservative.

In U.S. Pat. No. 5,263,274 Speed describes a game luring scent diffusing device made up of two containers with an interconnecting wick. The unit is suspended from a tree branch and scent fluid flow from one container, along the wick to the other container, where excess scent liquid is stored. A single container for scent liquid with a pull-out absorptive wick is disclosed by Eason in U.S. Pat. No. 5,622,314.

A deer scent dispenser that hangs from a tree, including a reservoir with a wick to disperse the scent, is disclosed by Jarvis in U.S. Pat. No. 5,307,584.

In U.S. Pat. No. 5,327,667 Fore discloses an absorbent pad with brittle container of scent fluid attached. The device is secured to a hunter's boot or clothing and the container ruptured to disperse the scent.

Cox, in U.S. Pat. No. 5,369,903, describes a deer lure employing urine from domestic goats, as well as using the goat urine in a "scent bomb".

A device that warms a liquid lure to disperse the scent in cold temperature conditions is disclosed by Porter in U.S. Pat. No. 5,429,271.

In U.S. Pat. No. 5,456,036 Butz shows an animal scent dispensing pistol that fires scent sticks of animal scent.

Baker et al., in U.S. Pat. No. 5,465,521, discloses a container with scent cartridges that a hunter may suspend from a branch to disperse scent at a hunting site.

A scent-releasing pole for attracting deer is disclosed by Fore in U.S. Pat. No. 5,555,665. The hollow pole contains several tapers impregnated with deer scent that are burned to release the scent to the air at a hunting site.

In U.S. Pat. No. 5,565,111 Newman describes a method of processing big game scent that includes filtration, heating or a combination of both to remove contaminants and pathogenic bacteria from liquid scent without destroying or denaturing the aromatic attractants.

Blaha, in U.S. Pat. No. 5,611,165, describes a hunting scent holder with an adsorbent pad for scents that seals for storage and opens for use in the field.

In U.S. Pat. No. 5,672,342 Bell discloses an animal scent attractant and cover scent kit made from urine collected from a single animal and packaged for storage prior to use.

Bruey, in U.S. Pat. No. 4,990,514, describes an insecticide bait that contains some Knox Brand Gelatin, plus numerous other components. Inazuka et al, in U.S. Pat. No. 4,160,824 discloses an insect attracting composition that contains gelatin plus numerous other components. Gelatin as one component for insect bait is disclosed by Hennart et al. in U.S. Pat. No. 4,205,066 and by Nesbitt et al in U.S. Pat. No. 4,487,759.

Thus, there exists an unmet need for a deer attractant material that produces a potent scent yet can be used repeatedly over time and transported easily to remote locations.

SUMMARY OF THE INVENTION

The invention is a semi-solid deer attractant lure comprising liquid deer urine and a sufficient amount of flavorless gelatin to produce a semi-solid rubbery composition. The invention also includes a method of making a semi-solid deer attractant lure. The steps include mixing flavorless gelatin powder with liquid deer urine at ambient temperature to produce a first ambient temperature mixture. Liquid deer urine heated to 180° F. is added with stirring to the first ambient temperature mixture to dissolve essentially all of the gelatin therein, to produce a second warm lure mixture. The second warm lure mixture is cooled to produce a semi-solid rubbery consistency deer attractant lure that is sealed in an airtight container to maintain lure scent. Also disclosed is a method of using a semi-solid deer attractant lure. The steps include obtaining a semi-solid deer attractant lure composed of deer urine and flavorless gelatin, placing the attractant lure in a flat covered container to maintain lure scent, and opening the container to the atmosphere at a hunting site to expose the attractant lure therein, thereby attracting deer to the site.

DESCRIPTION OF THE PREFERRED EMBODIMENTS

During the fall, and particularly during the hunting season, it is desirable to use attractant lures to bring game animals to a selected hunting site. As mentioned above, with respect to deer, and especially the male of the species or the buck, a buck lure is often used to tempt the buck. The commercially available buck lures are liquids sold in small bottles that can be applied to the ground, foliage or other fabrics to bring the scent into the air at the hunting site. Spreading the liquid on the ground or foliage gives a one-time use. Likewise, the various scent bombs and the like are messy to use by the hunter.

The present invention is a game animal urine attractant composition, and more particularly a deer urine attractant composition, as well as a method of making and using the composition.

The composition of the deer lure is liquid deer urine combined with a sufficient amount of flavorless gelatin to produce a semi-solid rubbery consistency. The ratio of liquid deer urine to flavorless gelatin is preferably about 256 to 1 on a weight basis, and most preferably the ratio is about 16 to 1 on a weight basis. There is sufficient gelatin present to maintain the semi-solid rubbery consistency of the lure, even at moderate temperatures, up to about 50° F. The 256 to 1 weight basis ratio of liquid deer urine to flavorless gelatin is sufficient to produce a material of the proper consistency. The semi-solid material maintains a strong lure scent over time, provided the lure is sealed in a suitable container. It is preferred that the container is air tight and have a generally flat shape to present a large upper surface area relative to the total volume of the lure in the container. It is also preferred that the deer urine used in the composition be from a female deer, thus attracting male deer to the lure. Deer urine is available from game farms, or the commercially available urine in small bottles may be used. Flavorless gelatin is available from numerous retail outlets such as grocery stores.

Once the attractant lure is prepared and placed in the container, it is best to store the sealed container under refrigeration to maintain a potent scent when the container is opened to the atmosphere at a hunting site to attract deer. The invention composition is particularly useful in that the container and lure therein can be moved from site to site with little difficulty, or resealed and used at later dates as desires.

The invention also includes a method of making a semi-solid deer attractant lure. For the most preferred composition, the steps include mixing one-quarter ounce of flavorless gelatin powder with two ounces of liquid deer urine at ambient temperature to produce a first ambient temperature mixture. This first mixture has a weight ratio of liquid to gelatin of 8 to 1. Two ounces of liquid deer urine heated to 180° F. is added with stirring to the first ambient temperature mixture to dissolve essentially all of the gelatin therein, to produce a second warm lure mixture. This second mixture has a weight ratio of liquid to gelatin of 16 to 1. The second warm lure mixture is cooled to produce a semi-solid rubbery consistency deer attractant lure that is sealed in an airtight container to maintain lure scent. It is preferred that the deer urine is from a doe or female deer.

Also disclosed is a method of using a semi-solid deer attractant lure. The steps include obtaining a semi-solid deer attractant lure composed of deer urine and flavorless gelatin, placing the attractant lure in a flat covered container to maintain lure scent, and opening the container to the atmosphere at a hunting site to expose the attractant lure therein, thereby attracting deer to the site. Again, it is preferred that the deer urine is from a doe or female deer.

While the invention has been particularly shown and described with reference to a preferred embodiment thereof, it will be understood by those skilled in the art that various changes in form and details may be made therein without departing from the spirit and scope of the invention.

I claim:

1. A semi-solid deer attractant lure composition comprising:

a) a deer attracting-effective amount of liquid deer urine; and b) flavorless gelatin in sufficient amount to produce and maintain a lure composition having a semi-solid, rubbery consistency, wherein the weight ratio of said liquid deer urine to said flavorless gelatin is from about 16:1 to about 256:1.

2. The composition according to claim 1, wherein said liquid deer urine is from a female deer.

3. A method of attracting deer comprising:

a) obtaining a semi-solid deer attractant lure composition comprising (i) a deer attracting-effective amount of liquid deer urine, and (ii) flavorless gelatin in sufficient amount to produce and maintain a lure composition having a semi-solid, rubbery consistency, wherein the weight ratio of said liquid deer urine to said flavorless gelatin is from about 16:1 to about 256:1;

b) placing said semi-solid deer attractant lure composition in a flat covered container to maintain lure scent; and c) opening said flat covered container to the atmosphere at a hunting site to expose said semi-solid deer attractant lure composition therein, thereby attracting deer to the site.

4. The method of claim 3, wherein said liquid deer urine is from a female deer.

* * * * *